United States Patent [19]

Blum et al.

[11] Patent Number: 5,109,121

[45] Date of Patent: * Apr. 28, 1992

[54] METHOD FOR RECOVERING RECOMBINANT PROTEINS

[75] Inventors: Galina Blum, Fairport, N.Y.; Ren-der Yang; Eun K. Lee, both of Terre Haute, Ind.

[73] Assignee: Pitman-Moore, Inc., Lake Forest, Ill.

[ * ] Notice: The portion of the term of this patent subsequent to Jan. 29, 2008 has been disclaimed.

[21] Appl. No.: 594,459

[22] Filed: Oct. 9, 1990

Related U.S. Application Data

[62] Division of Ser. No. 468,054, Jan. 22, 1990, Pat. No. 4,988,798.

[51] Int. Cl.⁵ ............................................. C07K 3/24
[52] U.S. Cl. .................................... 530/420; 530/399; 435/69.1
[58] Field of Search .................. 530/399, 350, 420; 435/69.1, 69.4

[56] References Cited

U.S. PATENT DOCUMENTS

| | | | |
|---|---|---|---|
| 3,624,251 | 11/1971 | Blum et al. | 530/350 |
| 4,857,317 | 8/1989 | Wiznendaele et al. | 424/89 |
| 4,988,798 | 1/1991 | Blum et al. | 530/399 |

*Primary Examiner*—Robert A. Wax
*Assistant Examiner*—Keith C. Furman
*Attorney, Agent, or Firm*—Wendell Ray Guffey; Thomas L. Farquer

[57] ABSTRACT

A method for recovering a recombinant protein from a protein solution containing high molecular weight contaminating proteins by directly adding Group IIA metal salts to the solution in amounts sufficient to selectively precipitate the high molecular weight protein contaminants is disclosed.

The high molecular weight precipitates are removed and the solution is further processed to remove low molecular weight contaminating proteins and other non-protein contaminants. The recombinant protein is subsequently recovered and further processed to produce a protein composition suitable for its intended use.

18 Claims, No Drawings

METHOD FOR RECOVERING RECOMBINANT PROTEINS

This application is a division of application Ser. No. 07/468,054, filed Jan. 22, 1990, now U.S. Pat. No. 4,988,798.

This invention relates generally to methods for recovering recombinant proteins and particularly to a method for recovering recombinant proteins from protein solutions containing high molecular weight contaminating proteins.

BACKGROUND OF THE INVENTION

Methods for producing recombinant proteins are well known in the art; heterologous DNA segments that encode for a particular protein are inserted into host microorganisms using recombinant DNA technology. By growing the transformant microorganisms under conditions which induce the expression of proteins, heterologous proteins such as insulin, somatotropins, interleukins, interferons, somatomedins, and the like can be produced.

Unfortunately, heterologous proteins produced by transformant microorganisms are frequently not biologically active because they do not fold into the proper tertiary structure when transcribed within the microorganism. The heterologous proteins tend to form aggregates which are recognizable within the cell as "inclusion bodies". These inclusion bodies may also be caused by the formation of covalent intermolecular disulfide bonds which link together several protein molecules to form insoluble complexes. The inclusion bodies generally contain mostly heterologous proteins and a small fraction of contaminating host microorganism proteins.

Several processes have been developed to extract the inclusion bodies from the microorganisms and convert the heterologous proteins contained therein into proteins having native bioactivity consistent with the natural parent or non-recombinant proteins. These processes generally involve disrupting the microorganism cell, separating the inclusion bodies from cell debris, solubilizing the inclusion body proteins in a denaturant/detergent which unfolds the protein, separating the heterologous inclusion body proteins from insoluble contaminants, removing the denaturant/detergent thereby allowing the heterologous proteins to refold into a bioactive tertiary conformation, and separating the protein from the contaminating proteins that remain in solution. Several recombinant protein purification schemes following this general procedure are known in the art: U.S. Pat. Nos. 4,511,503 and 4,518,526 to Olson et al and U.S. Pat. Nos. 4,511,502 and 4,620,948 to Builder et al disclose multi-step methods wherein (1) inclusion bodies are solubilized in a strong denaturant and a reducing agent, (2) insoluble contaminants are removed from the solubilized protein solution, (3) the strong denaturant is replaced with a weak denaturant, (4) the protein is allowed to refold assisted by oxidation of the sulfhydryl groups to disulfide bonds using molecular oxygen and a catalyst, typically metal cations or sodium tetrathionate and (5) the protein is separated from other contaminating proteins by membrane separation techniques or chromatography procedures. Rausch et al, U.S. Pat. No. 4,677,196, incorporated herein by reference, discloses a particular method for purifying and activating proteins which is a variation of the general scheme described above. The method comprises solubilizing the inclusion bodies in SDS, removing the excess SDS from the solution using dialysis or other suitable technique, chromatographing the SDS-protein solution on an ion-retardation resin, and chromatographing the resulting solution on an anion-exchange resin to recover the protein. All these known procedures share a common problem. The protein solution produced when the denaturant/detergent is removed contains the recombinant protein, low molecular weight contaminating proteins, non-protein contaminants, and high molecular weight contaminating proteins; the high molecular weight protein contaminants are often mostly dimers, oligomers and aggregates of the recombinant protein but also include non-recombinant proteins from the cell digest. It is often difficult, time consuming and expensive to separate the recombinant protein from these contaminants, particularly the recombinant protein dimers, oligomers and aggregates. Chromatographic and membrane separation techniques may be effective for separating the recombinant proteins from the contaminants but are cumbersome, lengthy, expensive and often give low percentage yields for protein recovery.

New and improved methods for easily, quickly and inexpensively recovering high yields of recombinant proteins from solutions containing high molecular weight protein contaminants are therefore needed.

SUMMARY OF THE INVENTION

It is, therefore, an object of the present invention to provide a new method for easily, quickly and inexpensively recovering high yields of recombinant proteins from protein solutions containing high molecular weight contaminating proteins.

It is another object of the present invention to provide a method for removing high molecular weight contaminating proteins from a recombinant protein solution thereby allowing the easy, quick and inexpensive recovery of the recombinant protein.

These and other objects are achieved by directly adding Group IIA metal salts to a solution containing high molecular weight contaminating proteins and a recombinant protein in amounts sufficient to selectively precipitate the high molecular weight protein contaminants. The compounds induce preferential precipitation of proteins having a molecular weight greater than about 1.5 times the molecular weight of the recombinant protein, particularly recombinant protein dimers, oligomers and aggregates having a molecular weight greater than about 1.5 times the molecular weight of the recombinant protein. The precipitates are separated from the solution leaving the recombinant protein, low molecular weight contaminating proteins and other non-protein contaminants in solution. The recombinant protein is recovered from the solution using known techniques and further processed to produce the desired protein product.

In the preferred embodiment, Group IIA metal salts are added directly to the solution in amounts sufficient to produce a 0.1–5% solution by volume. The high molecular weight contaminating proteins precipitate and are removed from the solution by conventional means such as filtration, centrifugation, and the like. The resulting protein solution containing the recombinant protein, low molecular weight contaminating proteins and other non-protein contaminants is further processed using conventional techniques such as chromatography to recover the recombinant protein.

Other objects, advantages and novel features of the present invention will become apparent from the following detailed description of the invention.

DETAILED DESCRIPTION OF THE INVENTION

The term "recombinant protein" as used herein defines a protein produced by recombinant techniques which one desires to recover in a relatively pure form and includes proteins having the amino acid sequence of native proteins and their analogs and muteins having substituted, deleted, replaced, or otherwise modified sequences.

The term "recombinant somatotropin" (rST) as used herein includes recombinant proteins having the amino acid sequence of native somatotropin, amino acid sequences substantially similar thereto, or an abbreviated sequence form thereof, and their analogs and muteins having substituted, deleted, replaced, or otherwise modified sequences. In particular, rST as used herein includes a protein of the same sequence as native somatotropin (ST), but having amino acids deleted from its amino terminal end. Examples of such proteins include but are not limited to delta-7 recombinant porcine somatotropin, delta-4 recombinant bovine somatotropin, and the like.

The term "high molecular weight contaminating proteins" or "high molecular weight protein contaminants" as used herein refers to proteins having a molecular weight greater than about 1.5 times the molecular weight of the recombinant protein, particularly recombinant protein dimers, oligomers and aggregates having a molecular weight greater than about 2 times the molecular weight of the recombinant protein.

The term "low molecular weight contaminating proteins" or "low molecular weight protein contaminants" as used herein refers to proteins having a molecular weight less than about 1.5 times the molecular weight of the recombinant protein.

The term "non-protein contaminants" as used herein refers to relatively low molecular weight substances such as precipitating agents, solubilizing agents, oxidizing agents, reducing agents, and the like which are typically in a protein solution.

According to the present invention, a method is provided for recovering a recombinant protein from a protein solution containing high molecular weight contaminating proteins. The method comprises directly adding Group IIA metal salts to the solution containing high molecular weight contaminating proteins and the recombinant protein in amounts sufficient to selectively precipitate the high molecular weight protein contaminants. The Group IIA metal salts preferentially induce the precipitation of proteins having a molecular weight greater than about 1.5 times the molecular weight of the recombinant protein, particularly recombinant protein dimers, oligomers and aggregates having a molecular weight greater than about 2 times the molecular weight of the recombinant protein. The method provides an improved method for easily, quickly and inexpensively recovering high yields of recombinant proteins from solutions containing high molecular weight protein contaminants.

In the preferred embodiment, a method is provided for recovering recombinant somatotropins (molecular weight about 20,000) by directly adding Group IIA metal salts to solutions containing high molecular weight contaminating proteins and recombinant somatotropins in amounts sufficient to selectively precipitate the high molecular weight protein contaminants. Group IIA metal salts preferentially induce the precipitation of proteins having a molecular weight greater than about 1.5 times the molecular weight of the recombinant somatotropin (molecular weight greater than about 30,000), particularly recombinant somatotropin dimers, oligomers and aggregates having a molecular weight greater than about 2 times the molecular weight of the recombinant somatotropin (molecular weight about 40,000 and up). The present method, therefore, provides a method for separating the recombinant somatotropin from its bioactive dimers, oligomers and aggregates.

Solutions containing a recombinant protein, non-protein contaminants, high molecular weight protein contaminants, and low molecular weight protein contaminants useful in the present invention are obtained by methods known in the art. Typically, protein inclusion bodies which have been produced by recombinant microorganisms are processed to remove lipids, and cell debris and the resulting relatively pure inclusion bodies containing recombinant protein and contaminating proteins, particularly high molecular weight recombinant protein dimers, oligomers and aggregates, are solubilized in a strong denaturant or detergent such as guanidine hydrochloride, sodium dodecyl sulfate (SDS), Triton, and the like.

The resulting protein solution is separated from any insoluble materials and the strong denaturant or detergent is removed to produce a protein solution containing the recombinant protein refolded into its native bioactive configuration, high molecular weight protein contaminants, low molecular weight contaminating proteins and other non-protein contaminants. Such solutions typically contain from about 1-50 mg/ml total protein and from about 0.05-4 mg/ml recombinant protein.

The polymer to monomer (P/M) ratio of the protein solution is calculated from a SUPEROSE-12 gel permeation chromatograph. The P/M ratio is an area ratio of high molecular weight protein contaminants to protein monomer and is thus a measure of purity of the solution. The solution needs to go through a "prepurification" step where P/M ratio is reduced to an extent (normally less than 0.5) that it can be introduced into DEAE SEPHAROSE column for further purification and processing into a final product. The present invention provides a method for removing the high molecular weight contaminating proteins while simultaneously achieving higher monomer recovery and a lower P/M ratio.

Group IIA metal salts are added to this solution according to the present invention to precipitate the high molecular weight contaminating proteins. The high molecular weight contaminating proteins that precipitate upon addition of the Group IIA metal salts are removed from the solution by conventional means such as filtration, centrifugation, and the like. The resulting protein solution containing the recombinant protein, low molecular weight contaminating proteins and other non-protein contaminants, if any, is further processed, as needed, to remove low molecular weight contaminating proteins and other non-protein contaminants such as precipitating agents, solubilizing agents, oxidizing agents, reducing agents, and the like. Typically, such non-protein contaminants are removed by dialysis, chromatography, or other suitable means whereas the low molecular weight contaminating proteins are separated from the protein by ion-exchange or other forms of chromatography.

The protein solution is further processed to produce a protein or protein composition suitable for its intended use, typically by lyophilization. These methods are well known in the art.

Group IIA metal salts useful in the present invention include all salts of the elements in Group IIA of the Periodic Table: beryllium, magnesium, calcium, strontium, barium and radium. Preferred compounds include salts of magnesium, calcium, barium and strontium.

Most preferably, the compounds of the present invention include the sulfate ($SO_4$), chloride ($Cl_2$) and nitrate ($NO_3$) salts of magnesium, calcium, barium and strontium. Preferred compounds include anhydrous calcium sulfate ($CaSO_4$), $CaSO_4$ dihydrate, $CaSO_4$ hemihydrate, calcium chloride, calcium chloride dihydrate, calcium nitrate ($Ca(NO_3)_2$), calcium lactate, calcium formate, magnesium sulfate ($MgSO_4$), magnesium chloride ($MgCl_2$), barium chloride ($BaCl_2$) and strontium chloride ($SrCl_2$).

Although the amount of Group IIA metal salts needed to induce precipitation varies depending on protein concentration, protein characteristics, compound added, and the like, the Group IIA metal salts are typically added to the solution in amounts sufficient to produce from about a 0.1–10% by volume solution of the compound, preferably from about a 1–5% solution by volume.

Recombinant proteins recoverable using the method of the present invention can be any protein having a molecular weight greater than about 5000 which are produced by recombinant microorganisms, typically in inclusion bodies. These include somatotropins, insulins, somatomedins, somatostatins, prolactins, placental lactogens, and the like.

Most preferably, recombinant somatotropins (molecular weight about 20,000) are recovered using the method of the present invention. The recombinant somatotropin can be a recombinant somatotropin from any species but are preferably bovine, porcine, avian, ovine, or human recombinant somatotropin, most preferably porcine or bovine recombinant somatotropin.

Methods for producing these recombinant proteins are well known in the art: For example, U.S. Pat. Nos. 4,604,359 and 4,332,717 disclose methods for producing human recombinant somatotropin; U.S. Pat. No. 4,431,739 discloses a method for producing recombinant somatotropins; E.P. Patent Application 0 104 920 discloses a method for producing recombinant porcine somatotropin; U.S. Pat. No. 4,443,359 discloses a method for producing recombinant bovine somatotropin; Schoner, *Biotechnology*, 3(2):151-54, discloses a method for producing recombinant somatotropin, and Buell, *Nucleic Acid Res.*, 13, 1923-38 (1985) discloses a method for producing recombinant somatomedin C.

Also, European Patent Application Publication No. 0 103 395 describes the construction of a transformant strain of *E. coli* containing a first plasmid which codes for delta 9 (Ser) bovine somatotropin (somatotropin less its 9 N-terminal amino acids and having an additional serine residue at the N-terminus) under the control of the lambda $P_L$ promoter-operator and which has a Shine-Dalgarno region derived from bacteriophage mu. The transformant also contains a second plasmid, pcI857, which codes for the production of the pcI857 temperature-sensitive repressor protein. The repressor protein can be inactivated by raising the temperature to about 42° C., thereby inducing expression of delta 9 (Ser) bovine somatotropin. A transformant strain of this type, *E. coli* HB101 ($P_L$-mu-delta 9 (Ser) bovine somatotropin and pcI857) has been deposited, with The American Type Culture Collection (ATCC), Rockville, Md. and assigned Accession No. 53030.

Construction of a similar transformant strain which codes for the production of delta 7 porcine somatotropin (porcine somatotropin less its first 7 N-terminal amino acids) is described in European Patent Application Publication No. 0 104 920. A transformant strain of this type, *E. coli* HB101 ($P_L$-mu-delta 7 porcine somatotropin and pcI857) has been deposited with ATCC and assigned Accession No. 53031.

Strains 53030 and 53031 are prolific producers of delta 9 (Ser) bovine somatotropin and delta 7 porcine somatotropin, respectively. In both instances, the expressed protein is sequestered within the cell in the form of insoluble, biologically inactive inclusion bodies which are visible under a microscope. Other methods for many similar proteins are known in the art.

In the preferred embodiment, a recombinant somatotropin solution containing from about 1–50 mg/ml total protein and from about 0.05–2 mg/ml recombinant somatotropin is treated with from about 1–5% $CaSO_4$ to precipitate the high molecular weight protein contaminants. The precipitate is removed by centrifugation and the recombinant somatotropin is recovered from the resulting solution using conventional means as described above.

Although the above recovery method is directed to recovering recombinant proteins, the method is equally applicable to separating and recovering non-recombinant proteins. For example, a solution containing a mixture of (1) a "useful or wanted protein", (2) high molecular weight proteins (molecular weight greater than about 1.5 times the molecular weight of the useful protein) and (3) low molecular weight proteins (molecular weight less than about 1.5 times the molecular weight of the useful protein) is treated according to the present invention to precipitate the high molecular weight proteins and thus separate the high molecular weight proteins from the useful protein and the low molecular weight proteins. The high molecular weight proteins are separated from the solution and discarded or further processed, as desired; the high molecular weight proteins can be recovered from the precipitate by redissolving the precipitate and recovering the proteins from the solution.

The useful protein is separated from the low molecular weight proteins by conventional means and further processed, if desired, to produce a protein product. The low molecular weight proteins which were separated from the useful protein are discarded or further processed, as desired. Typically, the low molecular weight proteins can be separated from the useful protein by chromatography or other means suitable for separating proteins having similar molecular weights. Many such protein separation means are well known to skilled artisans and are equally applicable in the present invention.

The invention having been generally described, the following examples are given as particular embodiments of the invention and to demonstrate the practice and advantages thereof. It is understood that the examples are given by way of illustration and are not intended to limit the specification or the claims to follow in any manner. In particular, inclusion bodies used in the experiments were prepared from transformed *E. Coli* strains which produce delta-7 porcine somatotropin. The inclusion bodies were isolated from *E. Coli* host strain HB101 transformed with a first plasmid ($P_L$-mu-delta-7 pST) coding for delta-7 pST and a second plasmid (pcI857) coding for the temperature sensitive lambda phage repression protein. Many other strains of microorganisms produce inclusion bodies containing many types of recombinant proteins which will function in the present invention. Similarly, methods for growing these microorganisms to produce inclusion bodies are well known in the art.

EXAMPLE 1

Recombinant porcine somatotropin (rpST) was recovered from microorganism inclusion bodies by (1) dissolving the inclusion bodies in sodium dodecyl sulfate (SDS) in carbonate buffer (25 mM $NaHCO_3$ and 21 mM $Na_2CO_3$), (2) removing insoluble contaminants from the solution, (3) adding an oxidizing agent for oxidation of rpST, and (4) removing the SDS from the solution to allow the rpST to refold into its bioactive configuration. The resulting protein solution contained the rpST, high molecular weight protein contaminants, low molecular weight contaminating proteins and other non-protein contaminants.

$CaSO_4 \cdot 2H_2O$ was added at 2.5% (w/v) concentration to the above refolded protein solution which contained 0.67 mg/ml of rpST monomer with a P/M ratio of 5.1 (pH 9.8 at 22°–25° C.) and mixed for 2 hours. The mixture was centrifuged at about x5000 G for 10 minutes to recover the supernatant. The rpST monomer and P/M ratio of the supernatant was analyzed by SUPEROSE-12 Fast Protein Liquid Chromatography. The result showed that the P/M ratio was reduced to 0.3 and that the monomer recovery was 83.0%. The data showed that the protein aggregate impurities and high molecular weight contaminating proteins were selectively precipitated by $CaSO_4 \cdot 2H_2O$ while leaving the monomers in solution.

EXAMPLE 2

Example 1 was repeated using other calcium salts: anhydrous $CaSO_4$, $CaSO_4$ hemihydrate, calcium nitrate ($Ca(NO_3)_2$) and calcium lactate. The results are shown in Table 1.

Referring to Table 1, the data shows that the aggregate impurities and high molecular weight contaminating proteins were selectively precipitated by the addition of these calcium salts.

EXAMPLE 3

Example 1 was repeated using alkaline metal salts of magnesium, barium and strontium. The results are shown in Table 1.

Referring to Table 2, the data shows that the aggregate impurities and high molecular weight contaminating proteins were selectively precipitated by these alkaline metal salts.

EXAMPLE 4

$CaCl_2 \cdot 2H_2O$ was added at 0.4% (w/v) concentration to the refolded protein solution in Example 1 which contained 0.4 mg/ml pST monomer with P/M ratio of 4.7 and mixed for about 30 minutes at room temperature 22°–25° C). The pH of the mixture was adjusted to about 9.0 and the supernatant of the mixture was collected after centrifuging at x5,000 G for 10 minutes. The resulting supernatant was analyzed by SUPEROSE-12 FPLC.

The result showed that the P/M ratio was reduced to 0.4 with a monomer recovery of 92.1%. This data shows that $CaCl_2 \cdot 2H_2O$ precipitates the protein aggregates and high molecular weight contaminating proteins selectively leaving monomers in solution.

EXAMPLE 5

The refolded protein solution in Example 1 was approximately 2x concentrated and diafiltered against 80 mM ethanolamine buffer at pH 9.0. To the diafiltered protein solution, which contained 0.67 mg/ml rpST monomer with P/M ratio of 3.5, $CaCl_2 \cdot 2H_2O$ was added at 0.4% (w/v) concentration and mixed for 30 minutes at 22°–25° C. The supernatant was separated by centrifuging at x5,000 G for 10 minutes. The supernatant was analyzed by SUPEROSE-12 FPLC.

The result showed the P/M ratio was reduced to 0.22 and a monomer recovery was 91.5%. This data shows that $CaCl_2 \cdot 2H_2O$ selectively precipitates the protein aggregates and high molecular weight contaminating proteins in an ethanolamine buffer system.

Obviously many modifications and variations of the present invention are possible in light of the above teachings. It is therefore to be understood that within the scope of the appended claims the invention may be practiced otherwise than as specifically described.

TABLE 1

| Calcium salt | Concentration [% (w/v)] | Initial P/M | Final P/M | Monomer Recovery (%) |
| --- | --- | --- | --- | --- |
| Anhydrous $CaSO_4$ | 2.5 | 3.0 | 0.03 | 87.3 |
| $CaSO_4$ hemihydrate | 2.5 | 3.6 | 0.05 | 83.7 |
| Calcium nitrate | 2.5 | 3.3 | 0.2 | 91.0 |
| Calcium lactate | 2.5 | 3.3 | 0.06 | 72.5 |

TABLE 2

| Salt | Concentration [% (w/v)] | Initial P/M | Final P/M | Monomer Recovery (%) |
| --- | --- | --- | --- | --- |
| $MgSO_4 \cdot 7H_2O$ | 2.5 | 3.0 | 0.1 | 71.0 |
| $MgCl_2$ | 1.0 | 3.0 | 0.3 | 92.0 |
| $BaCl_2$ | 1.6 | 3.7 | 0.5 | 50.0 |
| $SrCl_2 \cdot 6H_2O$ | 1.22 | 3.7 | 0.0 | 43.0 |

What is claimed is:

1. A method for recovering a recombinant protein from a protein solution containing high molecular weight contaminating proteins and the recombinant protein, comprising:

directly adding one or more Group IIA metal salts to the solution in amounts sufficient to selectively precipitate the high molecular weight contaminating proteins while leaving recombinant protein monomers in solution;

separating the precipitate from the solution; and recovering the recombinant protein from the solution.

2. The method of claim 1 wherein the total protein concentration of the solution is from about 1–50 mg/ml and the recombinant protein concentration of the solution is from about 0.05–4 mg/ml.

3. The method of claim 1 wherein the Group IIA metal salts are added directly to the solution in amounts sufficient to produce a 0.1–10% solution by volume.

4. The method of claim 1 wherein the Group IIA metal salts are selected from the group consisting of beryllium, magnesium, calcium, strontium, barium and radium salts.

5. The method of claim 4 wherein the Group IIA metal salts are selected from the group consisting of sulfate, chloride and nitrate salts.

6. The method of claim 1 wherein the Group IIA metal salts are selected from the group consisting of magnesium, calcium, strontium and barium salts.

7. The method of claim 6 wherein the Group IIA metal salts are selected from the group consisting of sulfate, chloride and nitrate salts.

8. The method of claim 1 wherein the Group IIA metal salts are selected from the group consisting of anhydrous calcium sulfate, $CaSO_4$ dihydrate, $CaSO_4$ hemihydrate, calcium chloride, calcium chloride dihydrate, calcium nitrate, calcium lactate, calcium formate, magnesium sulfate, magnesium chloride, barium chloride and strontium chloride.

9. The method of claim 1 wherein the high molecular weight contaminating proteins have a molecular weight of greater than about 30,000 and the recombinant protein to be recovered has a molecular weight of about 20,000.

10. A method for separating and recovering a protein from a protein solution containing the protein, high molecular weight proteins and low molecular weight proteins, comprising:
  directly adding one or more Group IIA metal salts to the solution in amounts sufficient to selectively precipitate the high molecular weight contaminating proteins while leaving recombinant protein monomers in solution;
  separating the precipitate from the solution; and
  recovering the recombinant protein from the solution.

11. The method of claim 10 wherein the total protein concentration of the solution is from about 1-50 mg/ml and the protein concentration of the solution is from about 0.05-4 mg/ml.

12. The method of claim 10 wherein the Group IIA metal salts are added directly to the solution in amounts sufficient to produce a 0.1-10% solution by volume.

13. The method of claim 10 wherein the Group IIA metal salts are selected from the group consisting of beryllium, magnesium, calcium, strontium, barium and radium salts.

14. The method of claim 13 wherein the Group IIA metal salts are selected from the group consisting of sulfate, chloride and nitrate salts.

15. The method of claim 10 wherein the Group IIA metal salts are selected from the group consisting of magnesium, calcium, strontium and barium salts.

16. The method of claim 15 wherein the Group IIA metal salts are selected from the group consisting of sulfate, chloride and nitrate salts.

17. The method of claim 10 wherein the Group IIA metal salts are selected from the group consisting of anhydrous calcium sulfate, $CaSO_4$ dihydrate, $CaSO_4$ hemihydrate, calcium nitrate, calcium chloride, calcium chloride dihydrate, calcium lactate, calcium formate, magnesium sulfate, magnesium chloride, barium chloride and strontium chloride.

18. The method of claim 10 wherein the high molecular weight contaminating proteins have a molecular of greater than about 30,000 and the protein to be recovered has a molecular weight of about 20,000.

* * * * *